United States Patent [19]

Lavender

[11] Patent Number: 4,565,073

[45] Date of Patent: Jan. 21, 1986

[54] FREEZING FRAME FOR A PLASMA CONTAINER

[75] Inventor: Ardis Lavender, Chappaqua, N.Y.

[73] Assignee: Armour Pharmaceutical Co., Tarrytown, N.Y.

[21] Appl. No.: 699,035

[22] Filed: Feb. 7, 1985

[51] Int. Cl.[4] ............................................. F25D 17/02
[52] U.S. Cl. ........................................ 62/373; 62/383; 62/457; 62/341; 206/425; 220/22.1
[58] Field of Search .................. 62/60, 383, 457, 373, 62/341; 206/425; 220/22, 22.1, 22.3; 249/132

[56] References Cited

U.S. PATENT DOCUMENTS

| | | | |
|---|---|---|---|
| 986,835 | 3/1911 | Lewis | 249/132 |
| 1,509,850 | 9/1924 | Thompson et al. | 62/60 |
| 1,511,824 | 10/1924 | Birdseye | 62/60 |
| 1,584,191 | 5/1926 | Petersen | 62/342 |
| 1,905,131 | 4/1933 | Birdseye et al. | 62/341 |
| 1,983,768 | 12/1934 | Norton | 62/60 |
| 2,260,450 | 10/1941 | Guinane | 62/60 |
| 2,261,839 | 11/1941 | Bergmann | 220/22.3 |
| 2,835,018 | 5/1958 | Guimont | 249/132 |
| 2,964,920 | 12/1960 | Staebler | 62/60 |
| 2,966,041 | 12/1960 | Zearfoss, Jr. et al. | 62/60 |
| 3,410,109 | 12/1968 | Maryland | 62/457 |
| 3,468,136 | 9/1969 | Swenson et al. | 62/64 |
| 3,554,429 | 1/1971 | Cohen | 220/22 |
| 3,875,754 | 4/1975 | Faust et al. | 62/60 |
| 3,898,023 | 7/1976 | Faust et al. | 62/64 |
| 3,971,231 | 7/1976 | Derry | 62/457 |
| 4,090,374 | 5/1978 | Faust et al. | 62/341 |
| 4,145,789 | 3/1979 | Morgan, Sr. | 220/22 |
| 4,194,369 | 3/1980 | Faust et al. | 62/60 |
| 4,251,995 | 2/1981 | Pert et al. | 62/60 |

*Primary Examiner*—Ronald C. Capossela
*Attorney, Agent, or Firm*—Scully, Scott, Murphy & Presser

[57] ABSTRACT

The Specification discloses a parallel-piped freezing frame having a plurality of compartments for freezing of flexible bags of plasma or other biological fluid. A slidable freezing plate is mounted within each compartment and cam means are provided for directing the freezing plate downwardly and laterally against a side wall of the component. The freezing plate and associated planar wall thereby mold the flexible bag into a flat but slightly wedge-shaped configuration. A freezing medium such as alcohol circulates through the freezing frame to freeze the contents of the flexible bag.

25 Claims, 10 Drawing Figures

FREEZING FRAME FOR A PLASMA CONTAINER

FIELD OF THE INVENTION

The present invention relates to the field of freezing biological fluids such as blood plasma, and particularly a freezing frame for supporting and molding containers of plasma during the freezing operation.

BACKGROUND OF THE INVENTION

The medical and health care professions have a real and pressing need for a method or means for packaging and preserving biological fluids or fluent components for future use. Much of the prior art teaches freezing biological fluids in a cryogenic medium which is expensive and requires sophisticated handling techniques to avoid a high-loss rate for the cryogenic medium. The prior art also demonstrates a need for maintaining a relatively uniform cross section of the material during the freezing operation to provide uniform and controllable freeze rates across the container to be frozen, and to prevent rupture and damage to cells. In addition, a frozen package of relatively uniform size and cross section greatly simplifies material handling and storage of the biological fluid. Three inch diameter round bottles are widely used at present for human plasma.

DESCRIPTION OF THE PRIOR ART

One family of patents, which include U.S. Pat. Nos. 3,875,754; 3,898,023; 4,090,374; and 4,194,369 to Faust et al. disclose a method and means for cryogenic freezing of fluid-filled pouches, including an expandable holder apparatus for flattening and freezing the fluid containing flexible pouches. U.S. Pat. No. 3,898,023 in particular discloses an apparatus for supporting flat parallel plates with a fluid-filled pouch placed there between in an upright position in a cryogenic freezing medium. The holder is particularly adapted to provide for expansion of the plates as necessary during the freezing of the biological fluid in the pouch. Applicant's invention may be contrasted with the teachings of this "family" of patents inasmuch as applicant does not require the use of a cryogenic medium, and has but a single moving part for each pouch to be frozen, thereby vastly simplifying the apparatus required for freezing the flexible pouches, and enabling the apparatus to be used in a wide variety of refrigerated environments.

U.S. Pat. No. 4,251,995 discloses a method for freezing human blood platelets in a glycerol-glucose solution using a statistically controlled cooling-rate device. This device also freezes a fluid-filled flexible pouch between metal plates which are immersed in a cryogenic medium. This apparatus also requires insulating plates between the pouch and the metal plates, and two separate pouches, one for the cryogenic media, and one for the biological fluid to be frozen. In contrast, applicant's device neither requires a cryogenic medium, nor requires the insulating plates for the flexible pouch. In addition, a single moving plate is used for positioning the flexible pouch during the freezing operation.

U.S. Pat. Nos. 1,584,191 and 2,835,018 disclose containers having a plurality of compartments for molding or freezing a product therein. These molds however do not provide slideable freezing plates, cam means or flexible pouch means for containing the biological fluid to be frozen.

U.S. Pat. No. 1,905,131 discloses a container having a plurality of parallel freezing plates that are displaceable laterally with respect to one another to contact a plurality of articles to be frozen. The device is substantially more complex and expensive than applicant's device which requires only a single sliding plate for each compartment to both form and freeze the fluid filled pouch.

U.S. Pat. No. 986,835 discloses a parallel-piped freezing frame having a plurality of compartments for freezing water into ice. This reference however does not utilize slideably disposed freezing plates therein, nor does it use a pouch for holding the fluid to be frozen.

U.S. Pat. Nos. 1,983,768 and 2,966,041 disclose freezing frames for a plurality of individual blocks of material to be secured between the frames, wherein plural frames are to be immersed in a separate refrigeration compartment. In the '041 patent, a flexible pouch is compressed between the wire frames to form ice cubes which are frozen in a conventional refrigerator. In the '768 reference, a plurality of frozen food containers are frozen in a brine solution. In each case, two separate plates are required, and in the '768 reference, a separate bag container is required to prevent contamination of the material to be frozen. In addition, while the discrete ice cubes disclosed in the '041 patent may be desirable from a consumer's stand point of view, they are undesirable from a biological stand point inasmuch as the differential areas of thickness result in differential freezing rates which causes rupture of cells.

U.S. Pat. No. 3,468,136 discloses a method for maintaining organs in a completely viable state when the refrigeration medium is alcohol.

OBJECTS OF THE INVENTION

It is therefore an object of the present invention to provide a freezing frame for suspending and molding a plurality of liquid-filled flexible bags within a freezing compartment wherein the flexible bags contain a biological fluid such as plasma or the like. The freezing frame is a parallel-piped having a plurality of compartments aligned therein with a vertically oriented planar wall defining one of the walls of each of the compartments. The slideably disposed freezing plate is mounted within the compartment for compressing and molding the flexible bag between the freezing plate and the planar wall. Cam means are provided between the side walls of the freezing compartment and the slideable freezing plate to guide the freezing plate downwardly and laterally towards the planar wall to thereby compress and flatten the flexible bag of plasma between the freezing plate and the planar wall. The slideably disposed freezing plate is mounted within the compartment for compressing and molding the flexible bag into a flat, but slightly wedge-shaped configuration between the freezing plate and the planar wall. A freezing medium such as isopropyl alcohol is then circulated through each of the compartments and the freezing frame to freeze the molded and compressed bag of plasma. The freezing frame be placed in a conventional deep freeze with isopropyl alcohol, or it may be immersed in another container with an alcohol dry ice bath. The bottom of the freezing frame is open so that a freezing medium can circulate freely throughout the compartments.

It is another object of the present invention to provide a parallelpiped freezing frame having a plurality of rows of compartments with a single slideable freezing plate mounted within each compartment. After assembling the parallelpiped, the assembly bolts may be further utilized as a guide means for the slideable freezing plate.

It is a further object of the present invention to provide an angled guide path for the freezing plate that enables the plate to slide downwardly and laterally when the flexible bag is inserted, and upwardly and away from when the bag is to be removed. The angled guide path provides a slightly wedge-shaped compartment for the enclosed flexible bag. The base of the wedge is located at the top of the freezing frame. This assures that the plate is easily moved upwardly when freezing is completed since the path of movement is tapered. By providing an angled cam path for the freezing plate, the normal freezing adhesion can be easily broken by sliding the plate upwardly and rearwardly away from the frozen and molded product. In addition, means are provided at the uppermost travel of the cam way to retain the freezing plate in its upward and outwardly displaced position while awaiting another flexible bag for molding and freezing.

It is a further object of the present invention to provide a simple and inexpensive apparatus which does not require the use of a cryogenic cooling medium to freeze flexible bags of plasma.

It is still a further object to the present invention to provide a freezing frame that will simultaneously mold and freeze a flexible bag of plasma to a linear shape and dimension to thereby facilitate material handling and storage of the frozen plasma.

DETAILED DESCRIPTION

Figure 1:
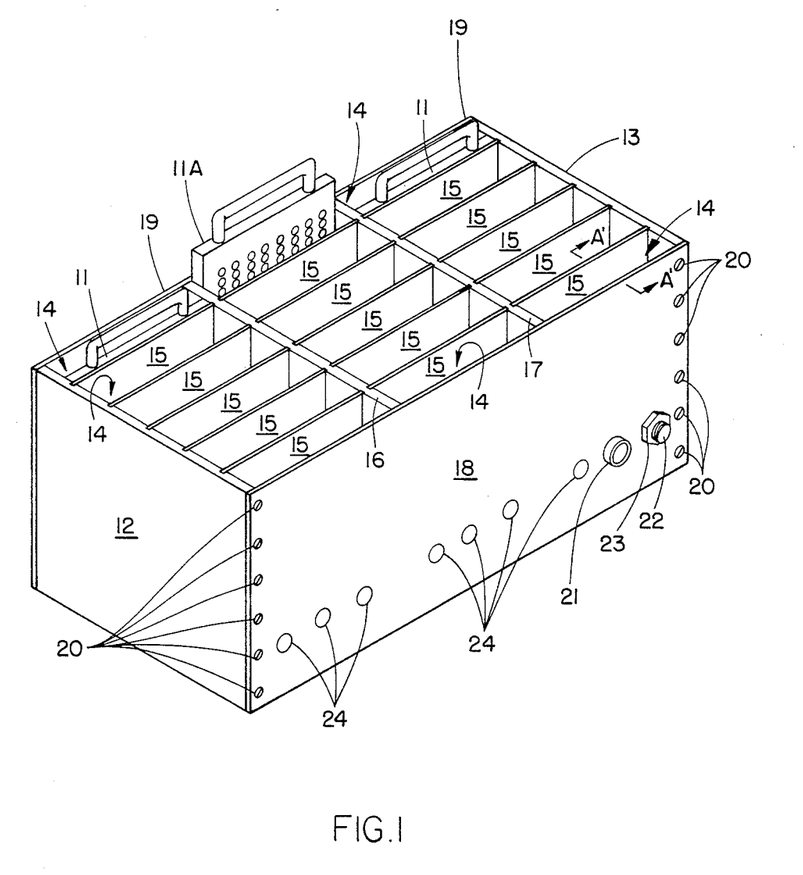
FIG. 1 is an isometric view of the freezing frame of the present invention having two freezing plates in the downwardly displaced position, and one freezing plate in an upward and open position.

FIG. 1 is an isometric view of the freezing frame of the present invention illustrating one freezing plate 11A in the upright open position and two freezing plates 11 in the downward and closed position. The remaining freezing plates have been eliminated in order simplify the drawing. As illustrated in FIG. 1, the freezing frame comprises a parallelpiped having a first 12 and a second 13 side wall with a plurality of compartments 14 defined there between. As illustrated in FIG. 1, two intermediate side walls 16 and 17 define 3 rows of compartments 14 with a single vertically extending planar wall 15 between each of the side walls. The freezing frame also defines a front wall 18 and a rear wall 19 that are parallel with the series of vertical planar walls 15. The front and rear walls 18, 19 are secured to the first and second side walls 12 and 13 by a plurality of screws 20. Alternately, the front and rear walls may be secured by a plurality of bolts or pipes passing through each of the compartments from front to rear as illustrated at 21, 22. As illustrated at 22, a solid bolt is used with a nut 23 to secure the front and rear plates with the intermediate side walls 16, 17 and the planar walls 15 there between. As illustrated at 22, a hollow pipe is used which may also be threaded on its exterior to receive a nut similar to that illustrated at 23 on bolt 22.

The freezing frame of the present invention may be cooled in any one of several ways. First, the freezing frame may be placed directly in a conventional freezer and cooled by air convection. Alternately, the frame may be placed in a freezer and filled with isopropyl alcohol as a cooling medium wherein the alcohol is cooled by convection and conduction through the walls of the freezing frames. In still another method, the frame is immersed in an insulated container which contains dry ice and isopropyl alcohol, or other suitable freezing medium.

Alternately, the freezing frame may be placed in an insulated container which is filled with isopropyl alcohol, and the alcohol cooled by an intermediate cooling medium circulated through a plurality of pipes 21 inserted through the apertures 24 and extending from the front to the rear of the freezing frame.

Accordingly, it is apparent that the freezing frame is a highly versatile device that may be used in an institutional environment, or in a portable environment wherein biological fluids being withdrawn at a remote location are quick-frozen for transport to a more permanent storage facility. The front and rear walls define a plurality of apertures 24, for receiving a pipe 21 or a bolt 22 for securing and aligning the frame and preventing distortion thereof. The frame may be secured by a conventional bolt 22 and nut 23 or by a pipe 21 which may also be threaded to receive a bolt similar to 23.

Figure 2:
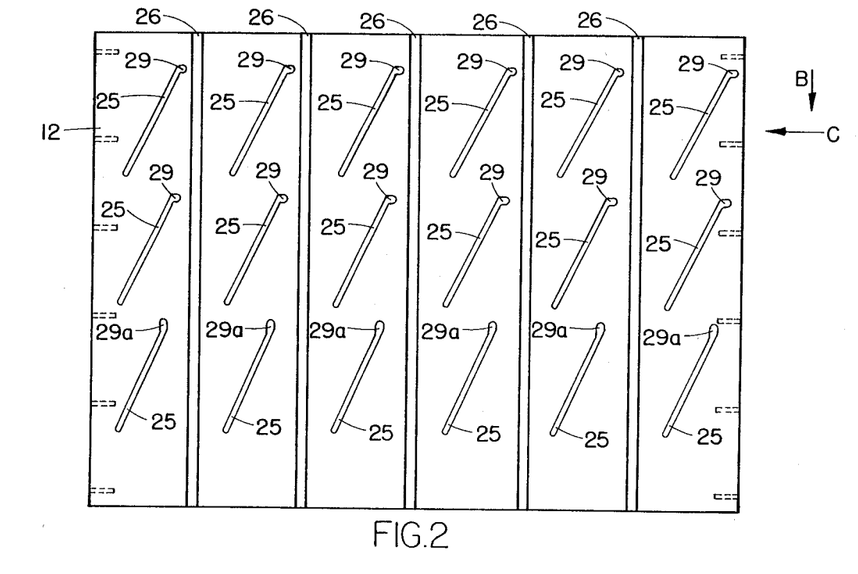
FIG. 2 is a plan view of one side wall that forms a portion of a parallelpiped illustrating the cam grooves fromed therein.
Figure 3A:
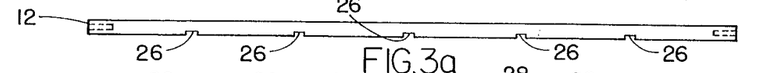
FIG. 3A is an end view of the side wall illustrated in FIG. 2.
Figure 3B:
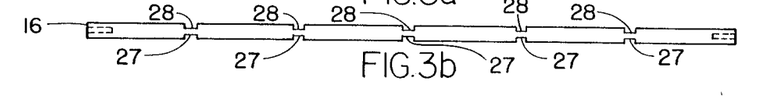
FIG. 3B is an end view of an intermediate side wall used in a container having a plurality of rows of compartments.
Figure 7:
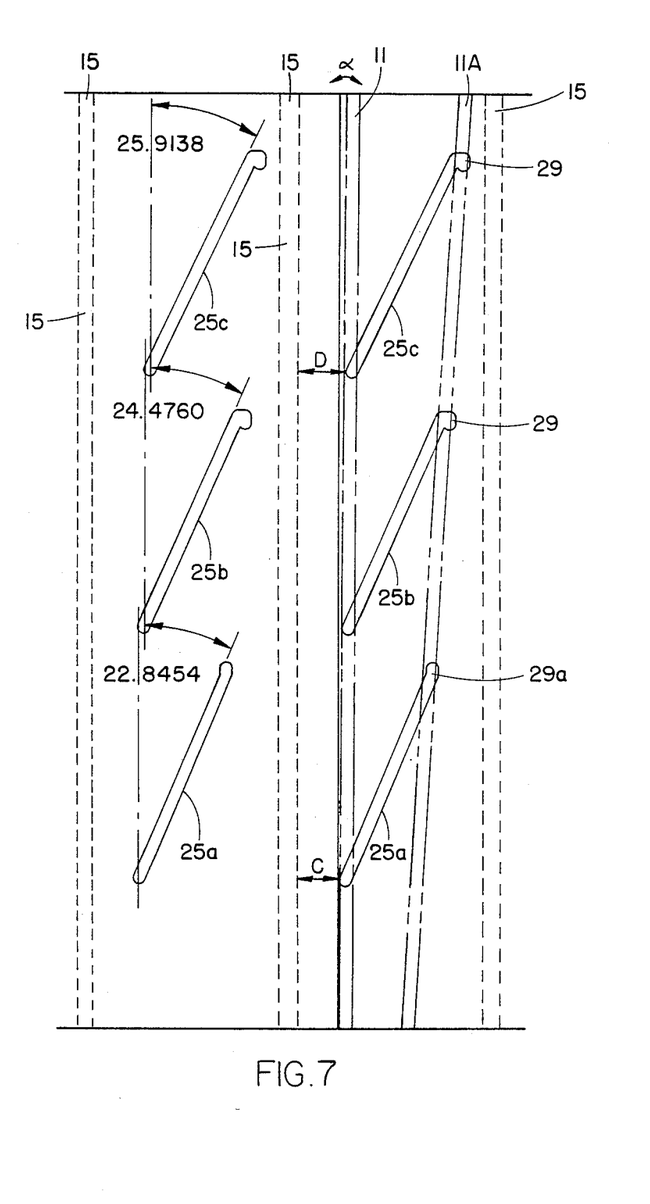
FIG. 7 is a diagrammatic end view of the side wall illustrated in FIG. 3 illustrating a means for molding a flattened, but slightly wedge-shaped frozed bag of plasma

FIG. 2 illustrates a configuration of side wall 12 and intermediate side wall 16 in planar and end views. As illustrated in FIG. 2, side wall 12 has a plurality of cam means which are defined as slots 25 for receiving and guiding each of the freezing plates after insertion of the fluid filled flexible bag. As illustrated in FIG. 2, the slots extend downwardly in the direction indicated by the arrow B and laterally in the direction indicated by the arrow C to bring the slideable freezing plate into engagement with the vertical planar walls which are fitted into slots 26 defined within the side wall. The intermediate side wall 16 has a pair of slots 27, 28 defined on opposite sides thereof for receiving a vertical planar wall on either side of the intermediate side wall. As illustrated in FIG. 7, the upper of the three slots is oriented with an angle greater than that of the middle slot. Similarly, the angle of the middle slot is greater than that of the lower slot. The upper, middle, and lower slot angles have angles of 25.9 degrees, 24.5 degrees, and 22.8 degrees respectively, and are displaced rearwardly relative to one another. Therefore, the freezing plate 11, with attached cam followers, will align at the bottom of the slots with approximately a one degree angle to the vertical. The slight differences in angles of the three slots assure that the plate will not be dislocated during the freezing process but will still be easily moved when the process has been completed.

With respect to cam means 25, the upper end of each cam surface on the top two rows of cams defines a horizontal portion 29 for receiving and holding the cam followers of the freezing plate in an upward and open position as illustrated at 11A in FIG. 1. The upper end of the cam surface of the bottom rows of cams defines a vertical portion which enhances the ability of the cam means to hold the plate in an upward and open position.

Figure 4:
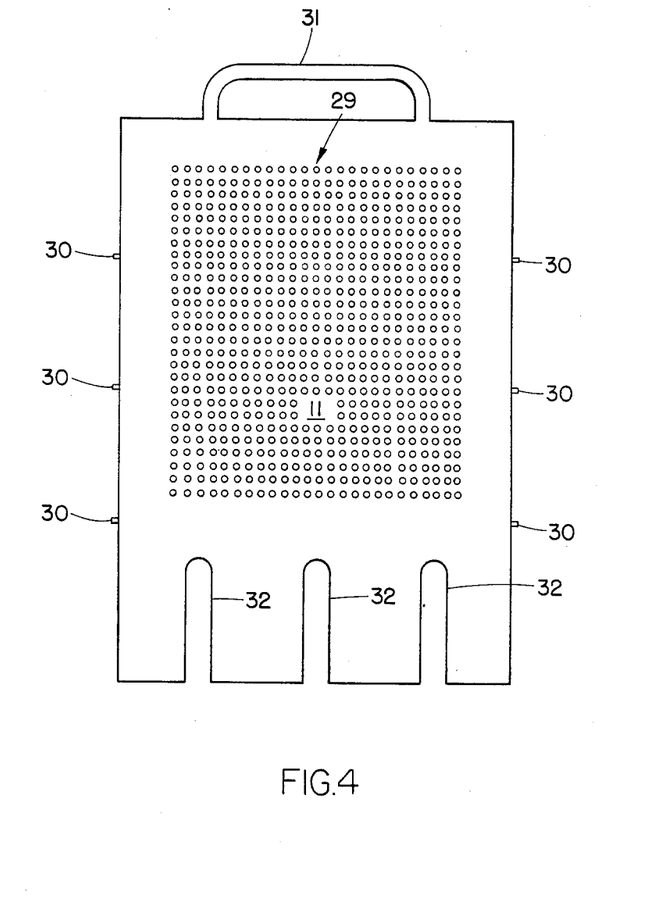
FIG. 4 is a planar view of the slideably disposed freezing plate used in the present invention.

FIG. 4 illustrates in planar view the slideable freezing plate 11 having a plurality of apertures 29 defined therein. The apertures 29 improve rate of heat conduction when flexible bags are enclosed by the plates. Plate 11 also defines on either side a plurality of cam followers 30 which are adapted to engage and follow the contour of grooves 25 defined in the first and second side walls 12, 13, and the intermediate side walls 16, 17.

Slideable freezing plate 11 is also equipped with a handle 31 for manual manipulation and a plurality of slots 32 that are aligned with the tubes or bolts 21, 22. These tubes or bolts provide several functions. First, they may structurally support the freezing frame; secondly, they may provide a cooling manifold for cooling the liquid refrigerant; third, they act as guide means for the slideable freezing plate 11. Finally, they initially act as a support for the bag of plasma within the freezing medium before molding by the freezing plate 11.

As illustrated in FIG. 7, the cam grooves 25 terminate at slightly different distances from the planar wall 15. As illustrated in FIG. 7 by arrow C, the bottom slot 25a terminates at a distance of approximately 0.54" from the planar wall 15 while the top slot 25c terminates at a distance of 0.67" from the planar wall. Thus, when a bag of plasma is compressed there between, it is flattened with a slight wedge-shaped configuration. With the above dimensions the wedge angle is (1°) one degree.

In addition, the horizontal portion 29 of the upper slot 25c is also offset from the vertical portion 29a of slot 25a. This provides an angle repose for the freezing plate when withdrawn to its upper position illustrated as 11A.

While three cam followers 30 have been described on each side of the slideable freezing plate 11, and three grooves have been provided as the cam means in each compartment, it is apparent that the number of grooves and cam followers could be varied and the configuration could also be altered to achieve the same purpose. For example, grooves 25 could be replaced with external ridges that would fit within slots defined in the outer edges of freezing plate 11. Alternately, rollers could be provided in lieu of the pins 30 illustrated in FIG. 4. The essential feature of the cam means defined by grooves 25 and pins 30 is that it guides the slideable freezing plate downwardly and laterally into engagement with the vertical planar wall 15 to thereby compress and flatten a flexible bag of fluid there between.

Figures 5, 6:
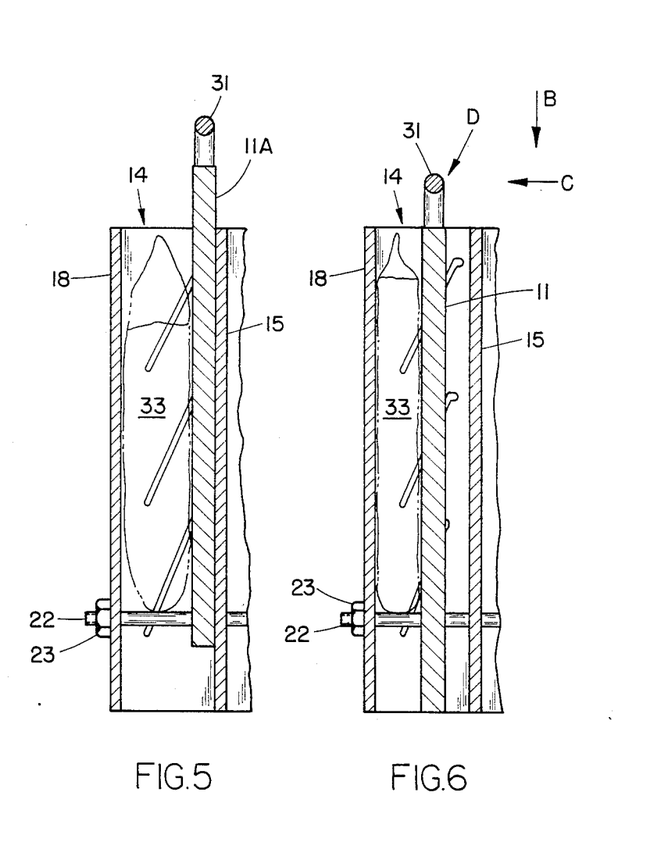
FIG. 5 is a diagrammatic cross section view illustrating the freezing plate in its upward and open position with a bag of plasma inserted therein.
FIG. 6 is a diagrammatic and cross sectioned view illustrating the freezing plate which has been displaced downwardly and laterally towards the planar side wall to thereby compress and mold a bag of plasma.

FIGS. 5 and 6 illustrate this compression along the cross section A—A' illustrated in FIG. 1. As illustrated, the front wall 18 has become the vertical planar wall for the compartment 14 into which has been placed a flexible bag of plasma 33. The slideable freezing plate 11 is suspended in its upward position (11A) by virtue of the pins 30 engaging the horizontal portion 29 of cam means 25 and by virtue of the pins 30 engaging the vertical portion 29a (illustrated in FIG. 2) of cam means 25. The flexible bag of plasma is lowered downwardly into the compartment 14 until it rests on bolts 22 as illustrated in FIG. 5. The slideable freezing frame is then urged laterally and downwardly as indicated by the letter D to thereby flatten and compress the flexible bag between the slideable freezing frame and the vertical planar wall 18 into a slightly wedge-shaped configuration. In the actual operation of the device, the rear wall of the container 15 illustrated in FIGS. 5 and 6 becomes the planar wall of the next compartment 14, against which will be sandwiched still another flexible bag of plasma 33.

Figure 8:
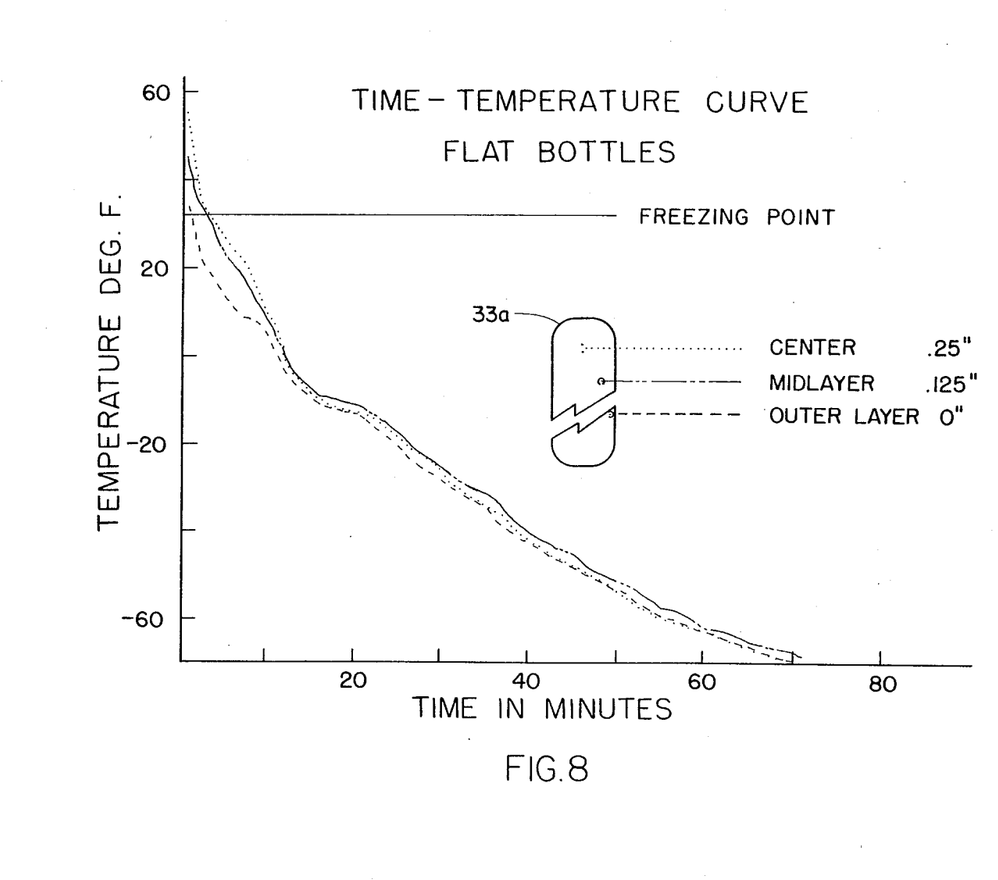
FIG. 8 is a comparative chart illustrating a time-temperature curve for freezing a bag of plasma as molded by the present invention.
Figure 9:
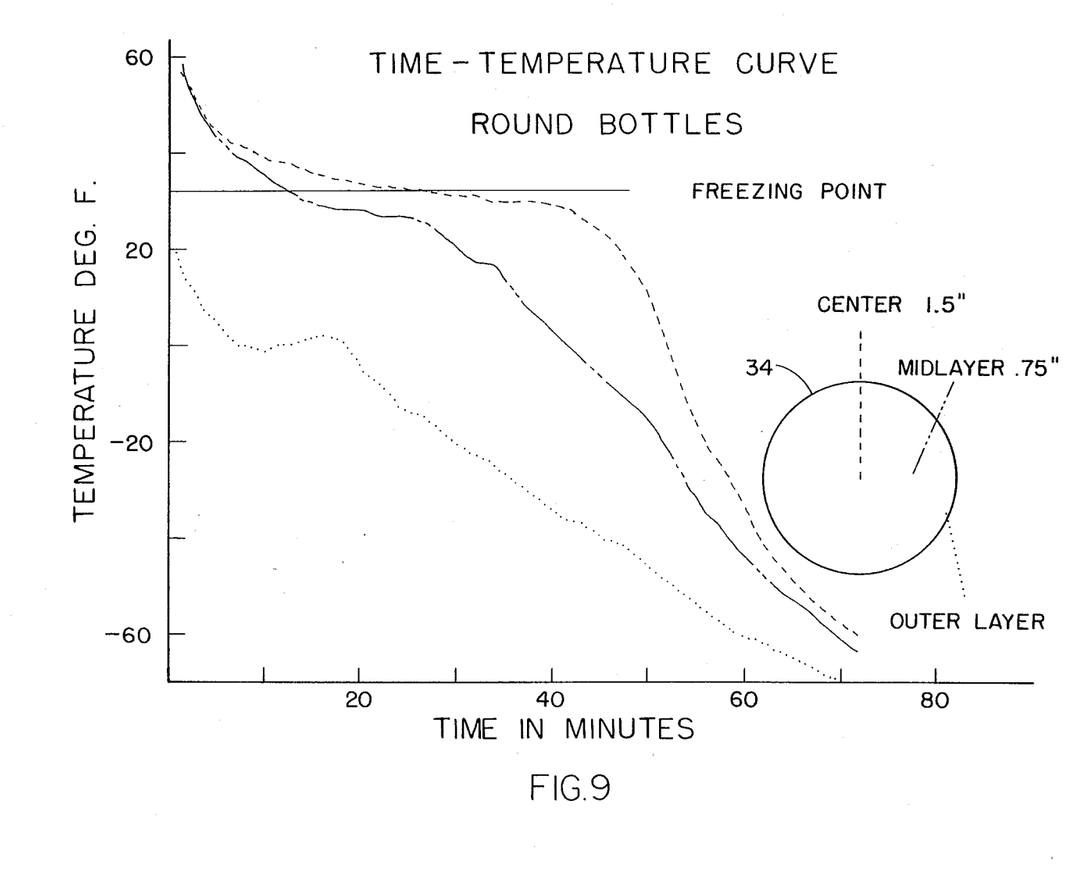
FIG. 9 illustrates a time-temperature curve for freezing a conventional bottle of plasma.

A comparison of the time temperature curves between flat bottles and conventional round bottles presently used for storing plasma is illustrated in FIGS. 8 and 9. As illustrated therein, a transducer was placed at the center, mid-layer, and outer-layer of both the flexible bag schematically illustrated as 33A (FIG. 8) and at the center, mid-layer and outer-layer of a round bottle 34 (as illustrated in FIG. 9). Both time-temperature curves were taken when isosmotic saline solutions were immersed in an isopropyl alcohol-dry ice bath. The time-temperature curve illustrated in FIG. 8 shows the response with the bags placed in the freezing frame. Iron-constantine thermocouples were placed at the outer-layer, at the mid-layer approximately 0.125 inches inwardly, and at the center, approximately 0.25 inches in. The temperature was monitored continously until it reached the temperature of the bath. As illustrated in FIG. 8, all three probes had reached freezing temperature within two minutes of immersion in the bath. From this point onward, there were only slight differences in temperature between the three probes.

A similar experiment is illustrated in FIG. 9 for round bottles. In these experiments, conventional three inch diameter bottles currently used for freezing of plasma, were filled with isosmotic saline and the probes were placed at the points indicated on the diagram. The central probe was one and a half inches from the outside of the bottle, the mid-layer probe was three quarters of an inch from the outside of bottle, and the outer probe was adjacent to the outer wall of the bottle. The central probe temperature did not reach freezing temperature until 26 minutes after immersion. The mid-layer probe reached freezing temperature within 14 minutes. The outer-layer probe was below freezing by the time the first measurement was taken.

A comparison of FIGS. 8 and 9 graphically demonstrates the advantages of the present invention and the use of the freezing frame with a flexible bag over the currently used prior art round storage bottles.

While the preferred embodiment of the present invention has been described and illustrated, and certain alternate configurations and construction had been described, it is obvious that various changes and modification can be made therein without departing the spirit of the present invention which should be limited only the scope of the appended following claims.

What is claimed is:

1. A freezing frame for suspending and molding a plurality of liquid filled flexible bags within a freezing compartment, said freezing frame comprising:
   (a) a parallelpiped frame having a first and a second side wall with a plurality of compartments defined there between, each of said compartments having a planar constraining wall extending between said first and second side walls
(b) a plurality of slideable freezing plates, with at least one plate mounted within each compartment,
(c) cam means defined between the walls of the compartment and the slideable plate for guiding each of said plates downwardly and laterally against said planar wall, whereby a flexible bag having a fluid to be frozen may be inserted within each compartment and flattened for quick freezing between said planar wall and its associated freezing plate.

2. A freezing frame as claimed in claim 1 wherein said cam means includes an angled groove in each of the side walls, and cam followers mounted on said freezing plate for following the contour of said grooves.

3. A freezing frame as claimed in claim 2 wherein three grooves are provided in each side wall with a separate cam follower for each groove mounted on said freezing plate.

4. A freezing frame as claimed in claim 3 wherein said grooves are angled downwardly and laterally toward said planar wall.

5. A freezing frame as claimed in claim 4 wherein each of the grooves are progressively angled at smaller angles from the vertical, with the uppermost groove having the largest angle.

6. A freezing frame as claimed in claim 5 wherein the lower most groove has a vertical portion defined at its uppermost extremity.

7. A freezing frame as claimed in claim 4 wherein the uppermost groove has a horizontal portion defined at its uppermost extremity for supporting said freezing plate in a first open position before insertion of the flexible bag.

8. A freezing frame as claimed in claim 1 wherein said cam means also terminates the travel of said freezing plates at a predetermined distance and predetermined angle from their respective planar walls.

9. A freezing frame as claimed in claim 8 wherein said predetermined angle creates a slightly wedge-shaped bag when said fluid therein is frozen.

10. A freezing frame as claimed in claim 1 said parallelpiped comprises front and rear co-planar walls that are parallel with a series of vertical planar walls, said front and rear co-planar walls being secured by a plurality of bolts that pass perpendicularly therethrough.

11. A freezing frame as claimed in claim 10 wherein each of said freezing plates defines a plurality of apertures therein.

12. A freezing frame as claimed in claim 10 wherein said freezing frame defines a plurality of rows of compartments with a common front and common rear wall, and at least one intermediate side wall mounted between said first and second said walls.

13. A freezer for shaping and freezing flexible bags of plasma, said freezer comprising:
(a) a parallelpiped freezing frame, said frame having a plurality of freezing compartments defined therein,
each of said compartments having at least one vertically oriented planar wall
(b) a slideable freezing plate mounted within each compartment for compressing and molding said flexible bag between said freezing plate and said planar wall
(c) cam means within each compartment for guiding said freezing plate downwardly and laterally towards the planar wall
(d) a freezing medium circulating through each of said compartments for freezing said plasma.

14. A freezer for shaping and freezing flexible bags of plasma as claimed in claim 13 wherein said cam means includes angle grooves in each of the side walls and cam followers mounted on said freezing plate for following the contour of said grooves.

15. A freezer for shaping and freezing flexible bags of plasma as claimed in claim 14 wherein three grooves are provided in each side wall with a separate cam follower for each groove mounted on said freezing plate.

16. A freezer for shaping and freezing flexible bags of plasma as claimed in claim 15 wherein said grooves are angled downwardly and laterally towards said vertical planar wall.

17. A freezer for shaping and freezing flexible bags of plasma as claimed in claim 16 wherein the uppermost groove has a horizontal portion defined at its uppermost extremity for supporting said freezing plate in a first open position before insertion of the flexible bag.

18. A freezing frame as claimed in claim 17 wherein each of the three grooves are progressively angled at smaller angles from the vertical, with the uppermost groove having the largest angle.

19. A freezer for shaping and freezing flexible bags of plasma as claimed in claim 18 wherein each of said freezing plates defines a plurality of slots that pass said bolts.

20. A freezer for shaping and freezing flexible bags of plasma as claimed in claim 19 wherein each of said freezing plates defines a plurality of slots for engaging said bolts.

21. A freezer for shaping and freezing flexible bags of plasma as claimed in claim 20 wherein said freezing frame defines a plurality of rows of compartments with common front and a common rear wall, and at least one intermediate side wall mounted between said first and second said walls.

22. A freezer for shaping and freezing flexible bags of plasma as claimed in claim 13 wherein the freezing medium is isopropyl alcohol.

23. A freezer for shaping and freezing flexible bags of plasma as claimed in claim 22 wherein said freezing media is an isopropyl alcohol dry-ice bath.

24. A freezing frame as claimed in claim 13 wherein said cam means also terminates the travel of said freezing plates at a predetermined distance and predetermined angle from their respective planar walls.

25. A freezing frame as claimed in claim 24 wherein said predetermined angle creates a slightly wedge-shaped bag when said fluid therein is frozen.

* * * * *